United States Patent [19]

McAfee

[11] 4,199,511
[45] Apr. 22, 1980

[54] CHLORENDIMIDOSILICON COMPOUNDS

[75] Inventor: Richard C. McAfee, Adrian, Mich.

[73] Assignee: SWS Silicones Corporation, Adrian, Mich.

[21] Appl. No.: 930,253

[22] Filed: Aug. 2, 1978

[51] Int. Cl.² ............................................... C07F 7/18
[52] U.S. Cl. ........................... 260/326 E; 252/2; 252/49.6; 252/63.7
[58] Field of Search ........................... 260/326 E

[56] References Cited

U.S. PATENT DOCUMENTS

| | | | |
|---|---|---|---|
| 3,558,741 | 1/1971 | Holub et al. | 260/326 E |
| 3,755,354 | 8/1973 | Holub et al. | 260/326 E |
| 3,770,768 | 11/1973 | Holub et al. | 260/326 E |
| 3,787,439 | 1/1974 | Holub et al. | 260/326 E |

*Primary Examiner*—Mark L. Berch

[57] ABSTRACT

Chlorendimidosilicon compounds of the formula

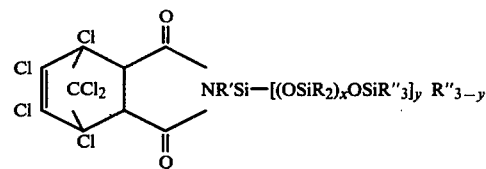

where R is a monovalent hydrocarbon radical or a substituted monovalent hydrocarbon radical, R' is a divalent hydrocarbon radical or a divalent hydrocarbonoxy radical in which the oxygen is in the form of an ether linkage, R" which may be the same or different is a monovalent hydrocarbon radical or a hydrocarbonoxy radical, x is a number of from 0 to 20,000, y is a number of from 0 to 3, and a process for preparing the same.

4 Claims, No Drawings

CHLORENDIMIDOSILICON COMPOUNDS

This invention relates to chlorendimidosilicon compounds, particularly to chlorendimidosilanes and siloxanes and more particularly to a process for preparing chlorendimidosilanes or siloxanes by reacting chlorendic anhydride with an amino-containing silane or siloxane.

SUMMARY OF THE INVENTION

The present invention relates to compounds corresponding to the formula:

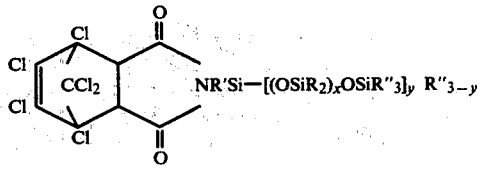

where R is a monovalent hydrocarbon radical having from 1 to 18 carbon atoms or a substituted monovalent hydrocarbon radical, R' is a divalent hydrocarbon radical having from 2 to 18 carbon atoms or a divalent hydrocarbonoxy radical in which the oxygen is in the form of an ether linkage, R" which may be the same or different is a monovalent hydrocarbon radical or a hydrocarbonoxy radical, x is a number of from 0 to 20,000 and y is a number of from 0 to 3.

DETAILED DESCRIPTION OF INVENTION

In the above formula the monovalent hydrocarbon radicals represented by R may be alkyl radicals, such as methyl, ethyl, propyl, butyl, hexyl, octyl and octadecyl radicals, cycloaliphatic radicals such as the cyclopentyl and cyclohexyl radicals, aryl radicals such as the phenyl radical, alkaryl radicals such as the ethylphenyl and butylphenyl radicals, and aralkyl radicals such as the tolyl, xylyl, phenylethyl, phenylbutyl radicals. Examples of substituted monovalent hydrocarbon radicals are the halosubstituted radicals described above such as the chloropropyl radicals and the cyanoalkyl radicals such as the cyanoethyl radical.

Examples of divalent radicals represented by R' are alkylene radicals such as ethylene, propylene, tetramethylene, pentamethylene, octamethylene, octadecamethylene and phenylene radicals. Suitable examples of divalent hydrocarbonoxy radicals having the formula (—C—C—O)$_n$ in which the oxygen is in the form of an ether linkage are (—C$_2$H$_4$O—)$_n$, (—CH$_2$OC$_2$H$_4$O—)$_n$ and (—C$_3$H$_6$O—)$_n$ radicals in which n is a number of from 1 to 10.

Suitable examples of monovalent hydrocarbon radicals represented by R" having up to 18 carbon atoms are alkyl radicals, such as methyl, ethyl, propyl, butyl, hexyl, octyl and octadecyl radicals, aryl radicals such as the phenyl radical, alkaryl radicals such as the ethylphenyl and butylphenyl radicals and aralkyl radicals such as the tolyl, xylyl, phenylethyl, phenylbutyl radicals. Preferred examples of hydrocarbonoxy radicals represented by R" are methoxy, ethoxy, propoxy, butoxy, octoxy and phenoxy radicals.

These novel silanes or siloxanes are prepared by reacting chlorendic anhydride of the formula

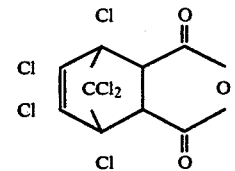

with an amino containing silicon compound of the formula

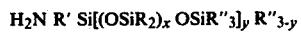

where R, R' R", x and y are the same as above, at a temperature of from about 50° C. up to 150° C. The reaction may be conducted in the presence or absence of an inert organic solvent. Examples of suitable solvents which may be employed are hydrocarbons such as hexane, heptane, octane and higher boiling paraffins, cyclohexane, toluene, xylene and chlorinated hydrocarbons.

Generally the reaction is conducted at a temperature of from 50° C. up to about 150° C. and more preferably at a temperature of from about 80° C. up to about 120° C. When the reaction is conducted in the presence of an inert hydrocarbon solvent, then it is preferably conducted at the reflux temperature of the solvent.

It is preferred that one mol of chlorendic anhydride be employed for each mol of amine. In carrying out the reaction, the chlorendic anhydride and the organosilicon compound are mixed together, preferably in the presence of an organic solvent, and the resultant mixture is heated to a temperature of from 50° C. up to the reflex temperature of the solvent for a period of time of from 3 to 18 hours. Upon completion of the reaction, the reaction mixture is distilled under reduced pressure to remove the solvent and water.

Examples of suitable amino containing organosilicon compounds which may be employed in the reaction with chlorendic anhydride are silanes of the formulas
H$_2$NC$_2$H$_4$Si(CH$_3$)$_3$,
H$_2$NC$_3$H$_6$Si(CH$_3$)$_3$,
H$_2$NC$_3$H$_6$Si(C$_2$H$_5$)$_3$,
H$_2$NC$_4$H$_8$Si(CH$_3$)$_3$,
H$_2$NC$_8$H$_{16}$Si(C$_3$H$_7$)$_3$,
H$_2$N(C$_2$H$_4$O)$_2$Si(CH$_3$)$_3$,
H$_2$N(C$_3$H$_6$O)$_4$Si(CH$_3$)$_3$,
H$_2$NC$_2$H$_4$Si(OCH$_3$)$_3$,
H$_2$NC$_2$H$_4$Si(CH$_3$)$_2$OCH$_3$
and the like. These silanes and their preparation are well known in the art.

Also siloxanes which may be reacted with chlorendic anhydride are those described in U.S. Pat. No. 3,890,269 to Martin. Specific examples of suitable siloxanes are those having the general formula

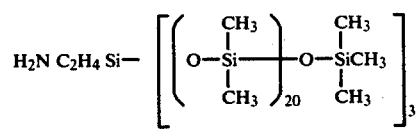

-continued

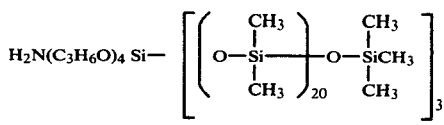

These siloxanes may be prepared by equilibrating a cyclic siloxane with an aminofunctional silicon compound in the presence of a basic catalyst and an aprotic solvent, if desired.

The chlorendimidosilanes and siloxanes of this invention may be used as lubricants, as dielectric fluids and as flame retardants for silicone elastomers.

The aminofunctional polysiloxane fluid used in the examples was prepared in the following manner:

Preparation of Aminofunctional Polysiloxane Fluid

A reactor containing 242 grams of eicosamethylnonasiloxane and 1.2 grams of potassium hydroxide is heated to 155° C. and a mixture containing 59.7 grams of aminopropyltriethoxysilane and 60 grams of water is added dropwise to the reactor with agitation. When the addition is completed, the reaction mixture is cooled to 100° C. and then 1.2 grams of acetic acid are added. The volatiles are removed under reduced pressure at a temperature up to about 175° C. and the product filtered. A clear transparent liquid is obtained having a kinematic viscosity of 26.4 cs. at 25° C. Nuclear Magnetic Resonance (NMR) analysis of the result product shows that the ratio of $CH_2N:CH_2:Si(CH_3)_2$ is 1:0.96:10.3.

In the following examples all parts are by weight unless otherwise specified:

EXAMPLE 1

About 123 parts of 1,4,5,6,7,7-hexachloro-endo-5-norbornene-2,3-dicarboxylic acid anhydride are added with agitation to a 1000 milliliter flask equipped with a condenser, Dean-Stark trap and containing 295 parts of an aminofunctional polysiloxane fluid whose preparation is described above and 212 parts of heptane. An increase in temperature is observed and the reaction mixture begins to thicken. The reaction mixture is refluxed at 96° C. for about two hours and then increased to about 100° C. and maintained at this temperature to about two hours. About 8 parts of water are collected in the Dean-Stack trap. The reaction mixture is distilled under reduced pressure (1 torr) for about two hours to remove the volatile materials. The residue is filtered and analyzed by NMR and IR. The product has a kinematic viscosity of 1,498 cst. at 25° C. and a dielectric strength of 420 volts/mil. After heating the product to a temperature of 200° C. in a forced-draft oven, it was found to be stable even after 1420 hours.

EXAMPLE 2

The procedure of Example 1 is repeated except that 370 parts of 1,4,5,6,7,7-hexachloro-endo-5-norbornene-2,3-dicarboxylic acid anhydride are added to a reactor containing 144 parts of trimethylaminopropylsilane and 100 parts of heptane with agitation. After heating for four hours at reflux temperatures, the volatiles are distilled off and the residue filtered. The residue is analyzed and shows a C:H:O:Cl:N:Si ratio of about 14:1:2:6:1:1 and the presence of an imide linkage.

EXAMPLE 3

The procedure of Example 1 is repeated except that 335 parts of 1,4,5,6,7,7-hexachloro-endo-5-norbornene-2,3-dicarboxylic acid anhydride are added with agitation to a reactor containing 200 parts of heptane and 2,573 parts of an aminofunctional polysiloxane fluid of the formula

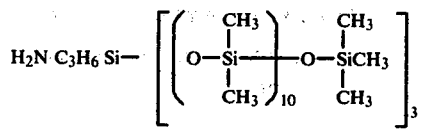

and heated to reflux temperature for eight hours. The volatile materials are removed under reduced pressure and the product filtered. The infrared spectrum indicates that the product contains an imide linkage. Elemental analysis shows a ratio of C:H:O:Si:Cl:N of 13.0:12.0:6.0:5.7:1.0:0.2.

EXAMPLE 4

About 168 parts of 1,4,5,6,7,7-hexachloro-endo-5-norbornene-2,3-dicarboxylic acid anhydride are added with agitation to a reactor containing 400 parts of heptane and 2,492 parts of an aminofunctional polysiloxane fluid having the formula

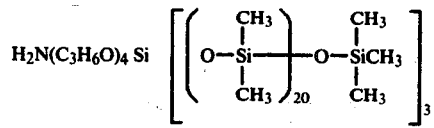

and heated to reflux temperature for eight hours. The volatile materials are removed under reduced pressure and the product filtered. Analysis of the product shows a ratio of C:H:O:Si:Cl:N of 24.5:67.0:11.5:11.0:1.0:0.2.

What is claimed is:
1. A compound of the formula

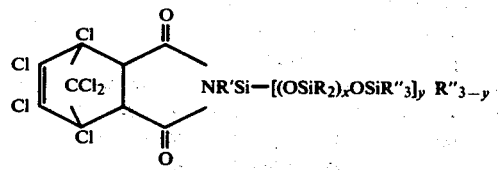

where R is selected from the class consisting of monovalent hydrocarbon radicals, halo-substituted monovalent hydrocarbon radicals and cyanoalkyl radicals having from 1 to 18 carbon atoms, R' is a divalent hydrocarbonoxy radical having the formula (—C—C—O—)$_n$ in which the oxygen is in the form of an ether linkage, R" is selected from the class consisting of monovalent hydrocarbon radicals and hydrocarbonoxy radicals having up to 18 carbon atoms, x is a number of from 0 to 20,000 and y is a number of from 0 to 3 and n is a number of from 1 to 10.

2. The compound of claim 1, wherein R is a monovalent hydrocarbon radical having from 1 to 18 carbon atoms.

3. The compound of claim 1, wherein y is equal to 0.

4. The compound of claim 1, wherein y is equal to 1.

* * * * *